(12) United States Patent
Lawrence et al.

(10) Patent No.: US 8,371,036 B2
(45) Date of Patent: Feb. 12, 2013

(54) METHOD AND TEMPLATE FOR PRODUCING A TENSILE TEST COUPON

(76) Inventors: Jason A. Lawrence, Owasso, OK (US);
James R. Perrault, Tulsa, OK (US);
Brian O'Connell, Tulsa, OK (US)

( * ) Notice: Subject to any disclaimer, the term of this patent is extended or adjusted under 35 U.S.C. 154(b) by 135 days.

(21) Appl. No.: 12/799,388

(22) Filed: Apr. 23, 2010

(65) Prior Publication Data

US 2011/0067500 A1    Mar. 24, 2011

Related U.S. Application Data

(63) Continuation-in-part of application No. 12/564,735, filed on Sep. 22, 2009.

(51) Int. Cl.
*G01B 3/14* (2006.01)
(52) U.S. Cl. ............................. 33/562; 33/529
(58) Field of Classification Search .................. 73/827; 33/562, 529; 408/72 R
See application file for complete search history.

(56) References Cited

U.S. PATENT DOCUMENTS

| 4,574,443 | A | 3/1986 | Persak et al. |
| 6,070,911 | A | 6/2000 | Namikawa et al. |
| 6,510,865 | B2 | 1/2003 | King et al. |
| 6,643,945 | B1 | 11/2003 | Starks |
| 2006/0191445 | A1 | 8/2006 | Stengel et al. |
| 2008/0152442 | A1 | 6/2008 | Barrett |

OTHER PUBLICATIONS

Zhao et al., "Effect of joint contamination on the quality of butt-fused high-density polyethylene (HDPE) pipe joints." NRCC-45337, Canadian Journal of Civil Engineering.
International Search Report and Written Opinion issued by the International Searching Authority (ISA/US) on Nov. 19, 2010 in PCT/US10/49621.

*Primary Examiner* — Lisa Caputo
*Assistant Examiner* — Jonathan Dunlap
(74) *Attorney, Agent, or Firm* — Gable Gotwals

(57) ABSTRACT

A method and template enable the testing of fusion joints of plastic pipes to be conducted by a single operator in the field at the welding site by the efficient and precise extraction from the joints to be tested of a number of high quality tensile coupons. The coupons are tested to failure in a field-suitable, well controlled, self contained, tensile testing apparatus. A narrowing bow-tie-like pattern of the coupon ensures that the failure of the coupon in the tensile test will occur at the narrowest section of the coupon. The template can be visually aligned with the joint to ensure that it is the joint that will be tested.

28 Claims, 12 Drawing Sheets

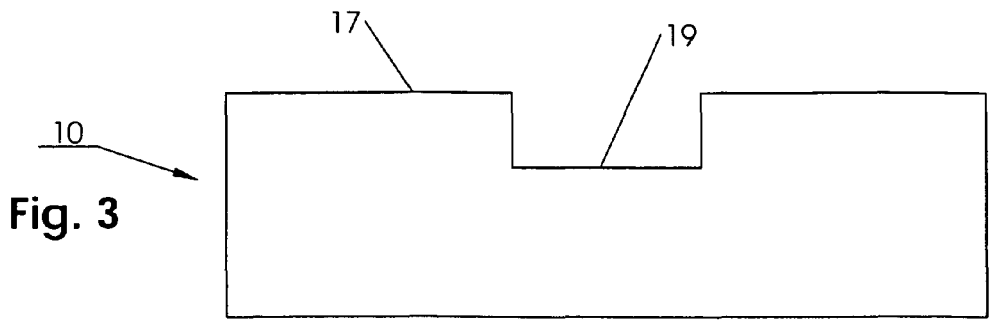
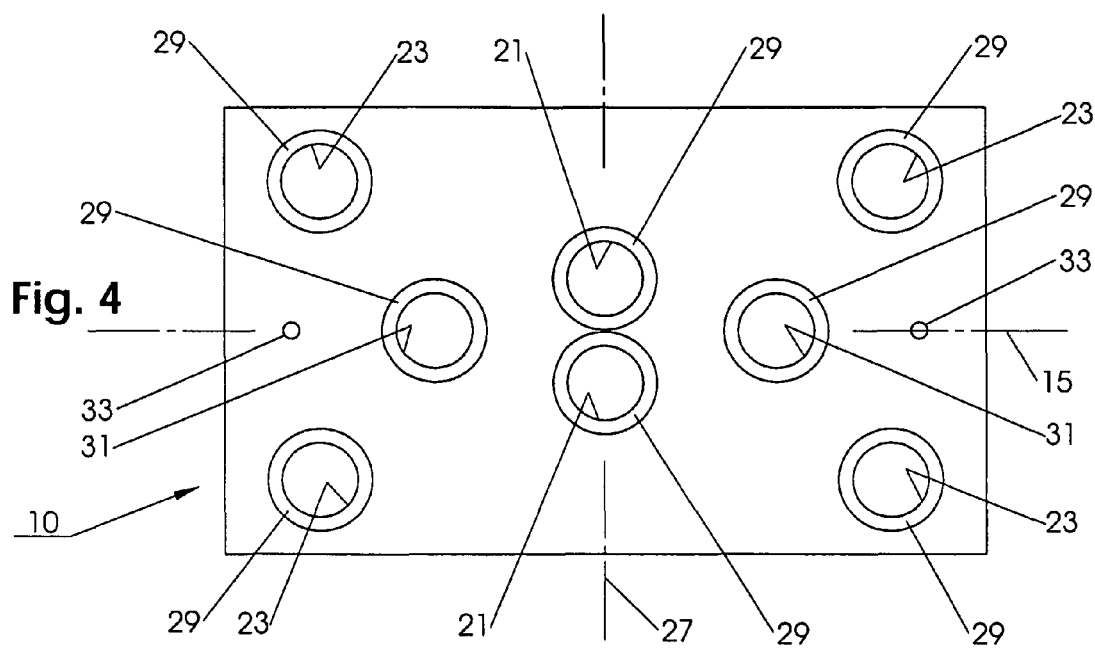
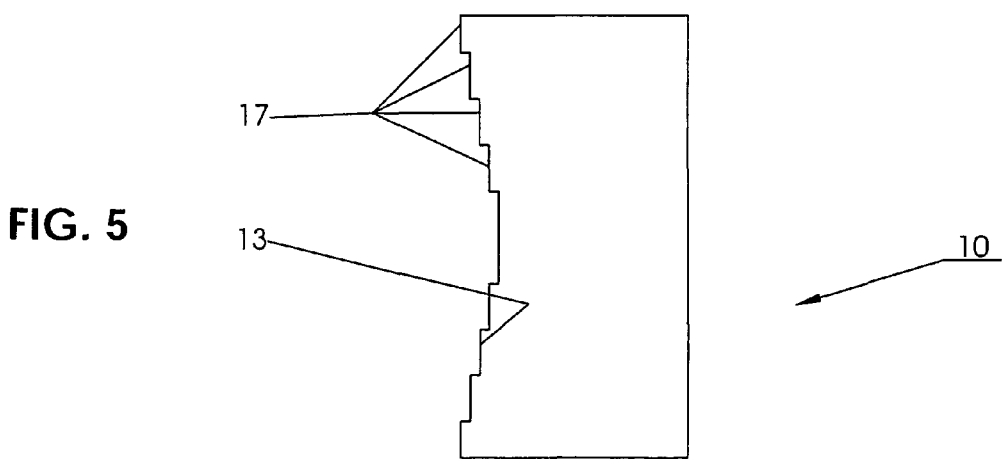

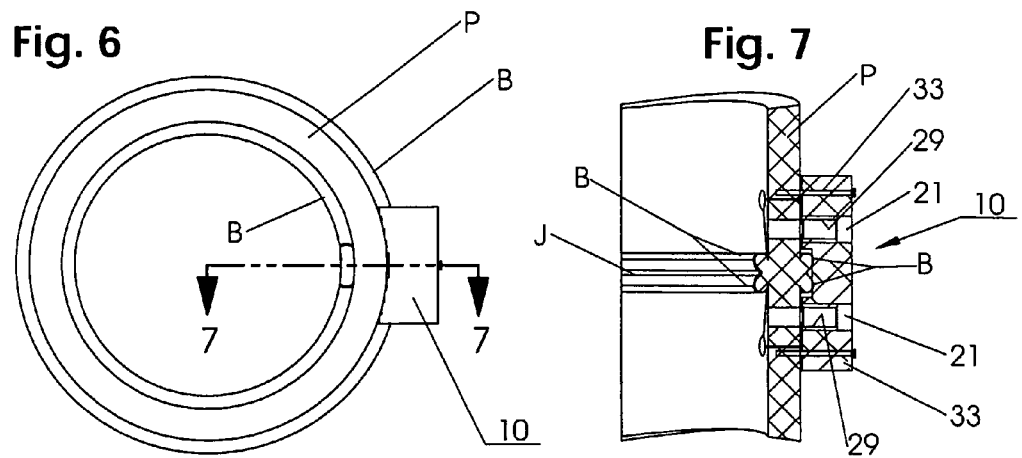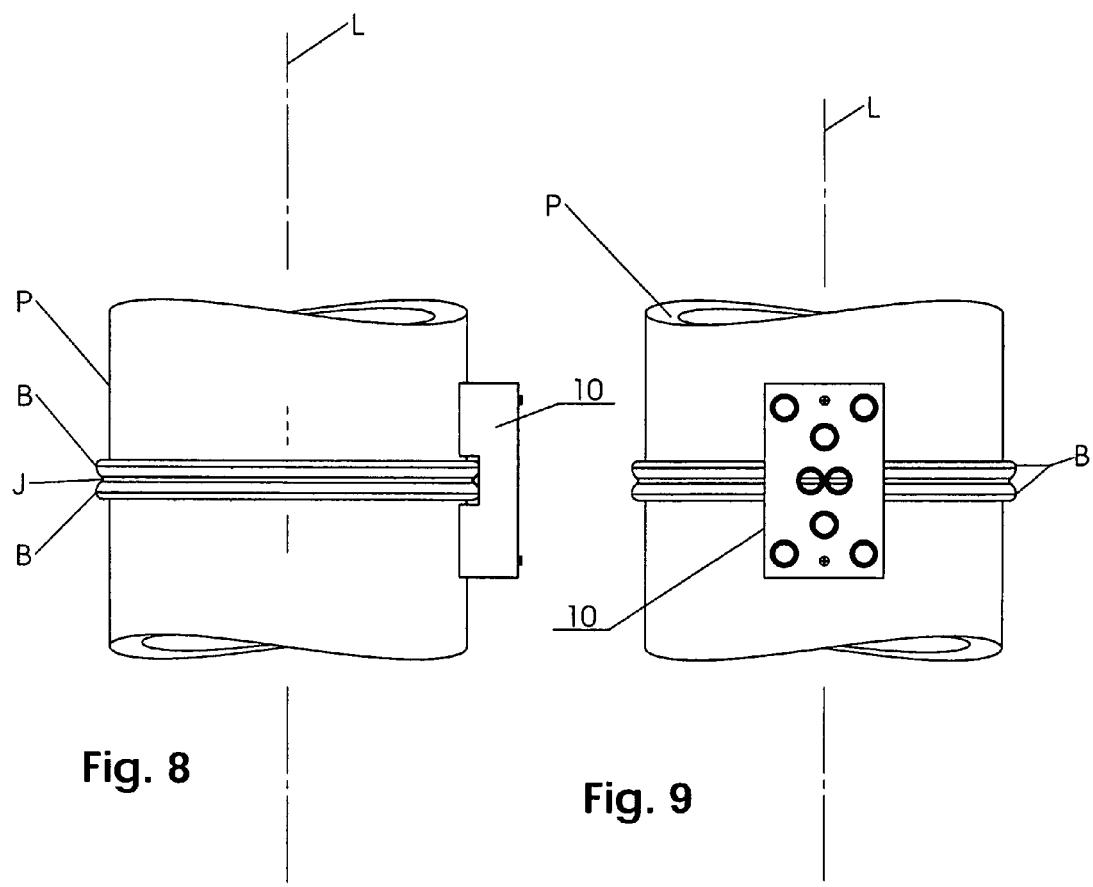

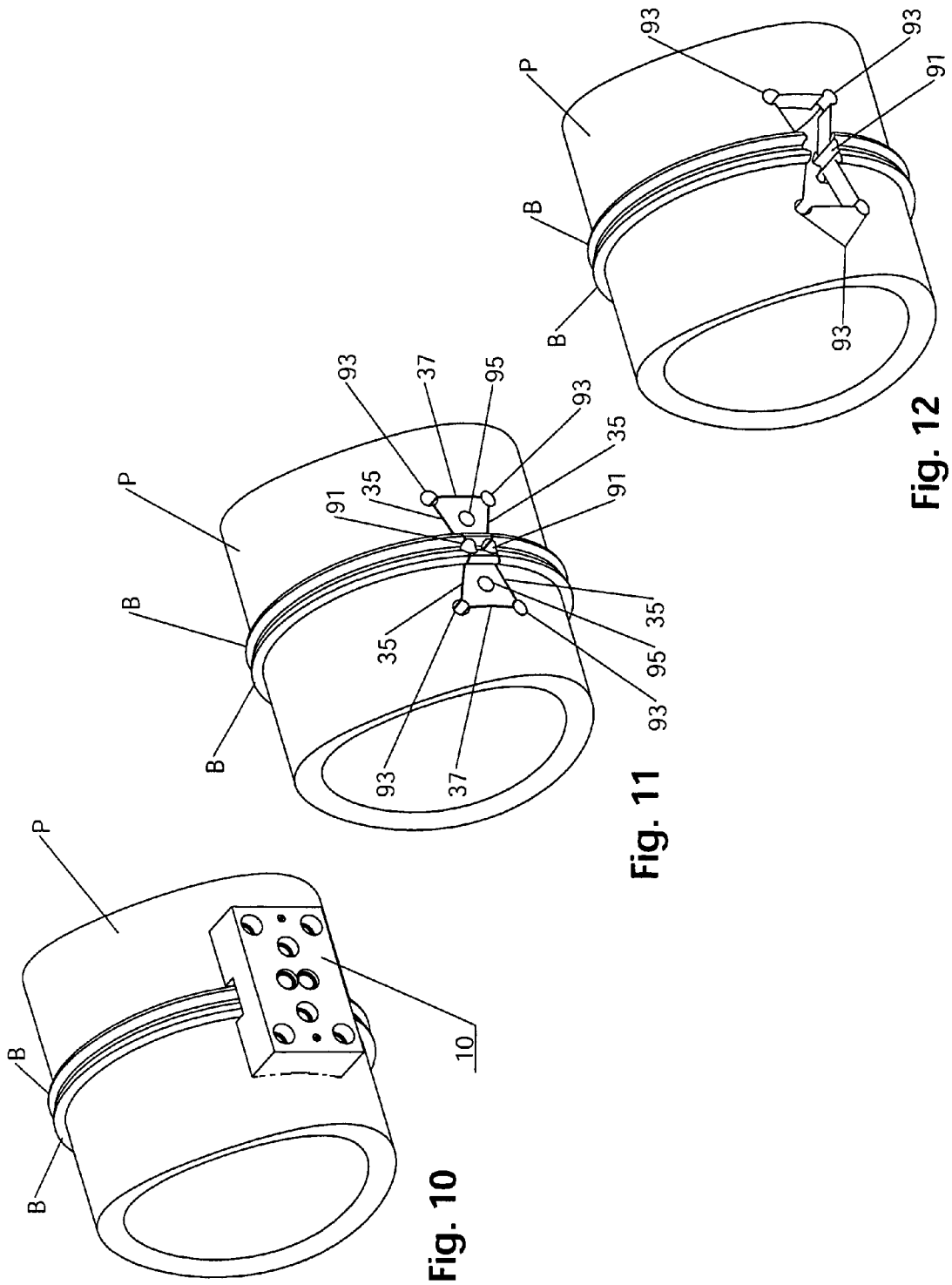

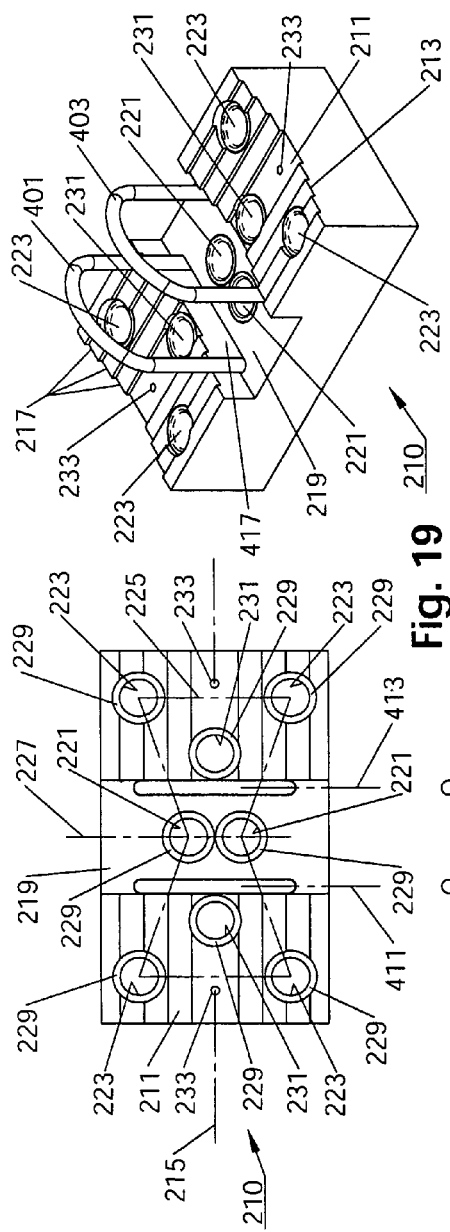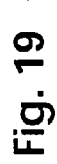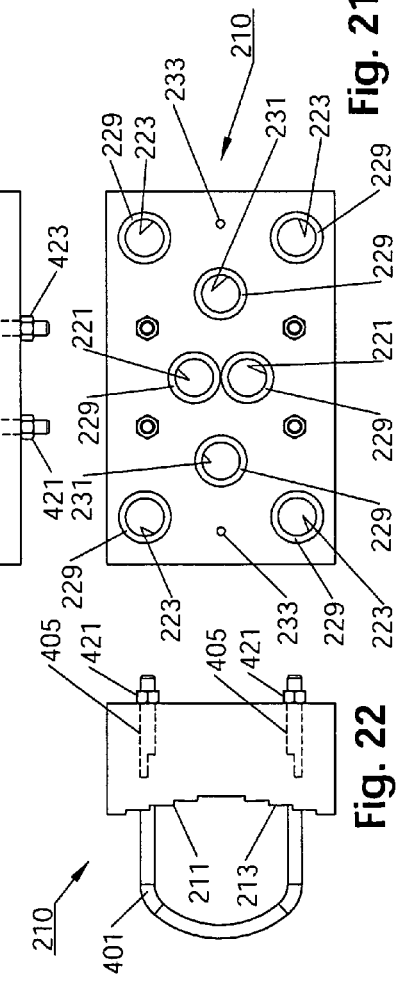

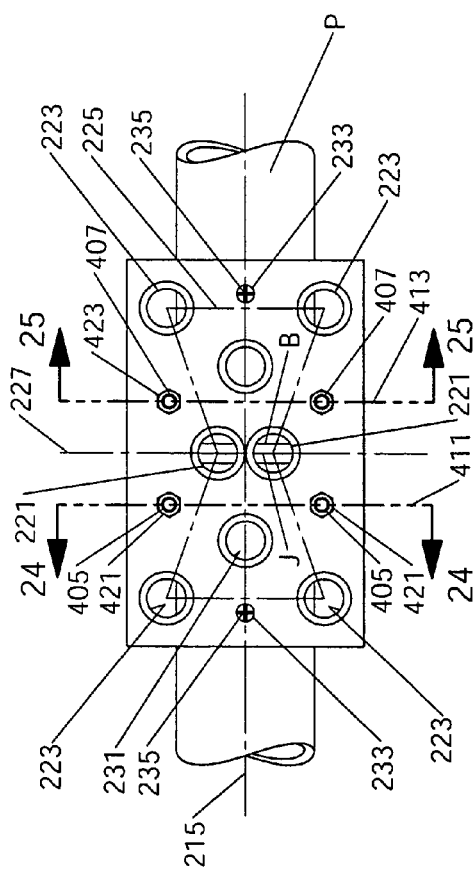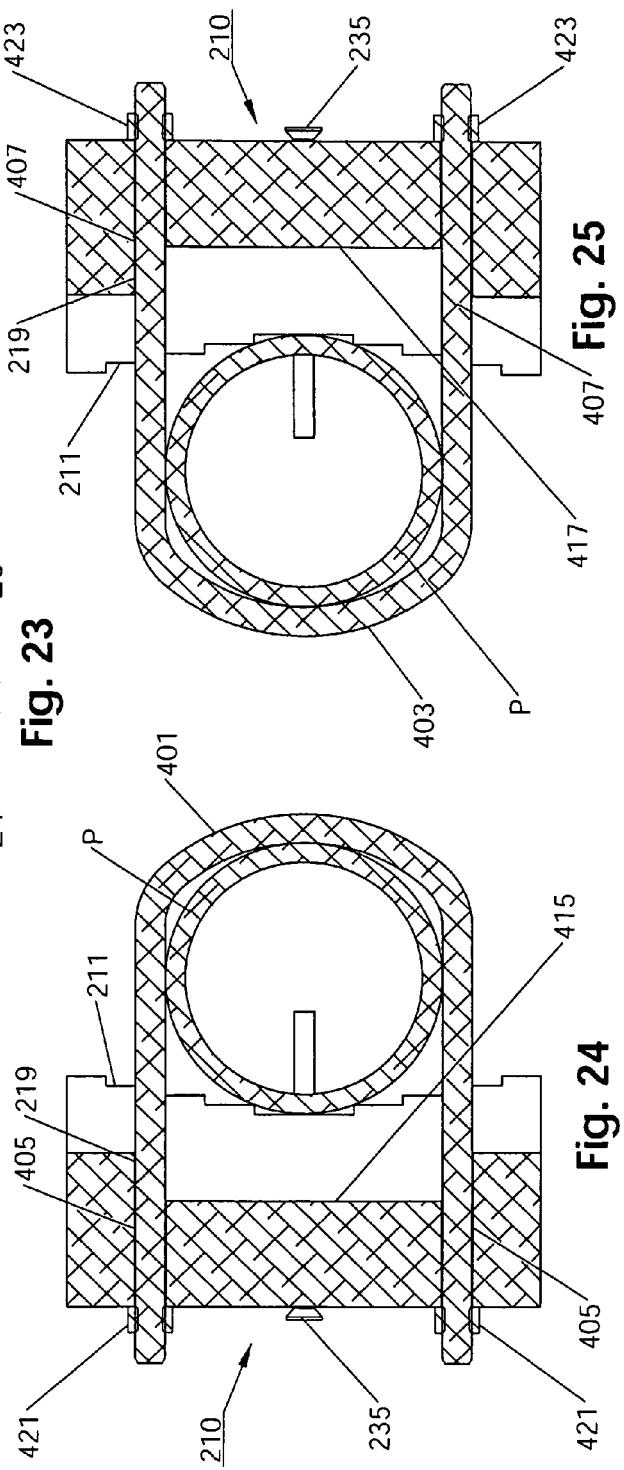

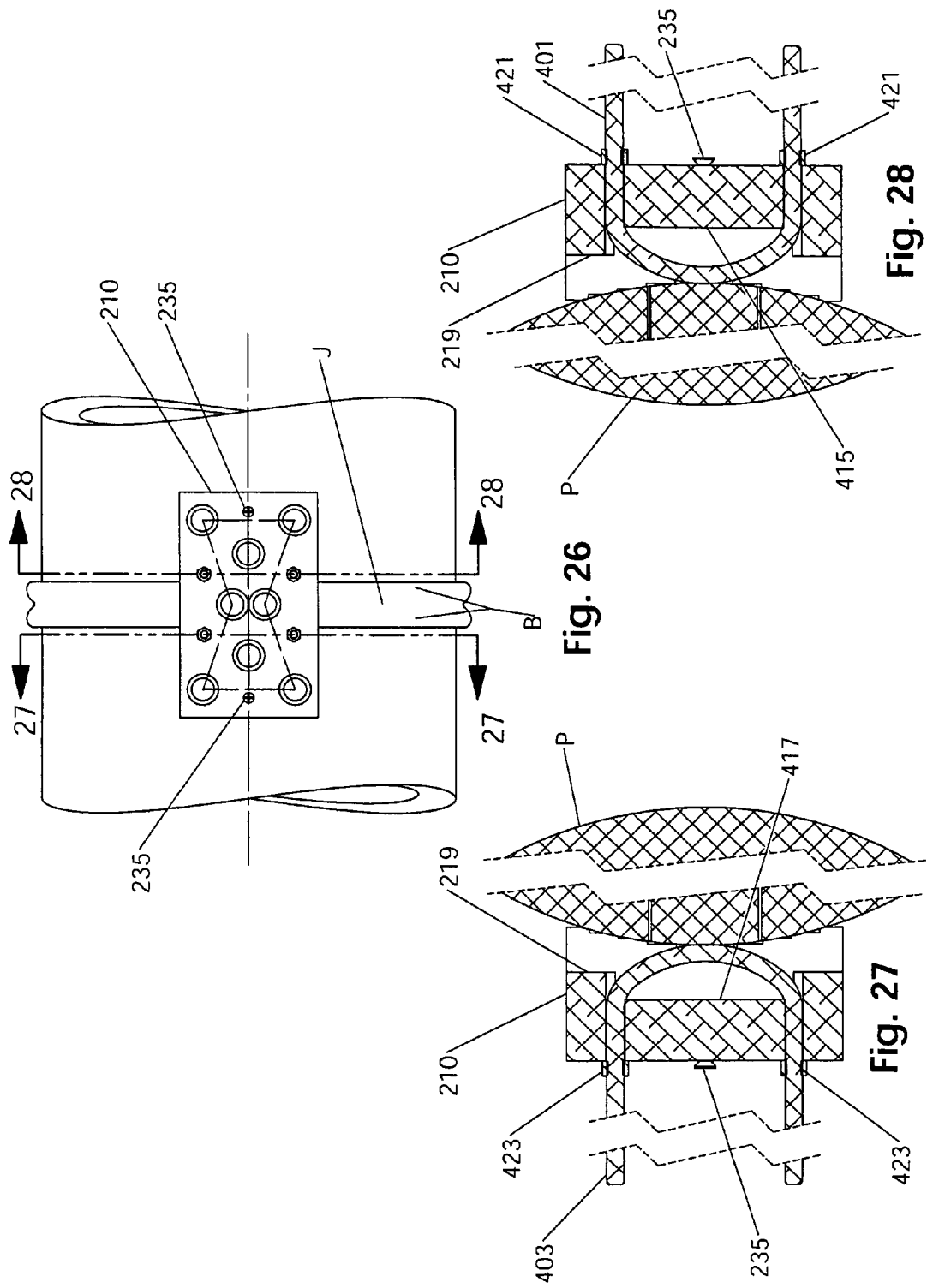

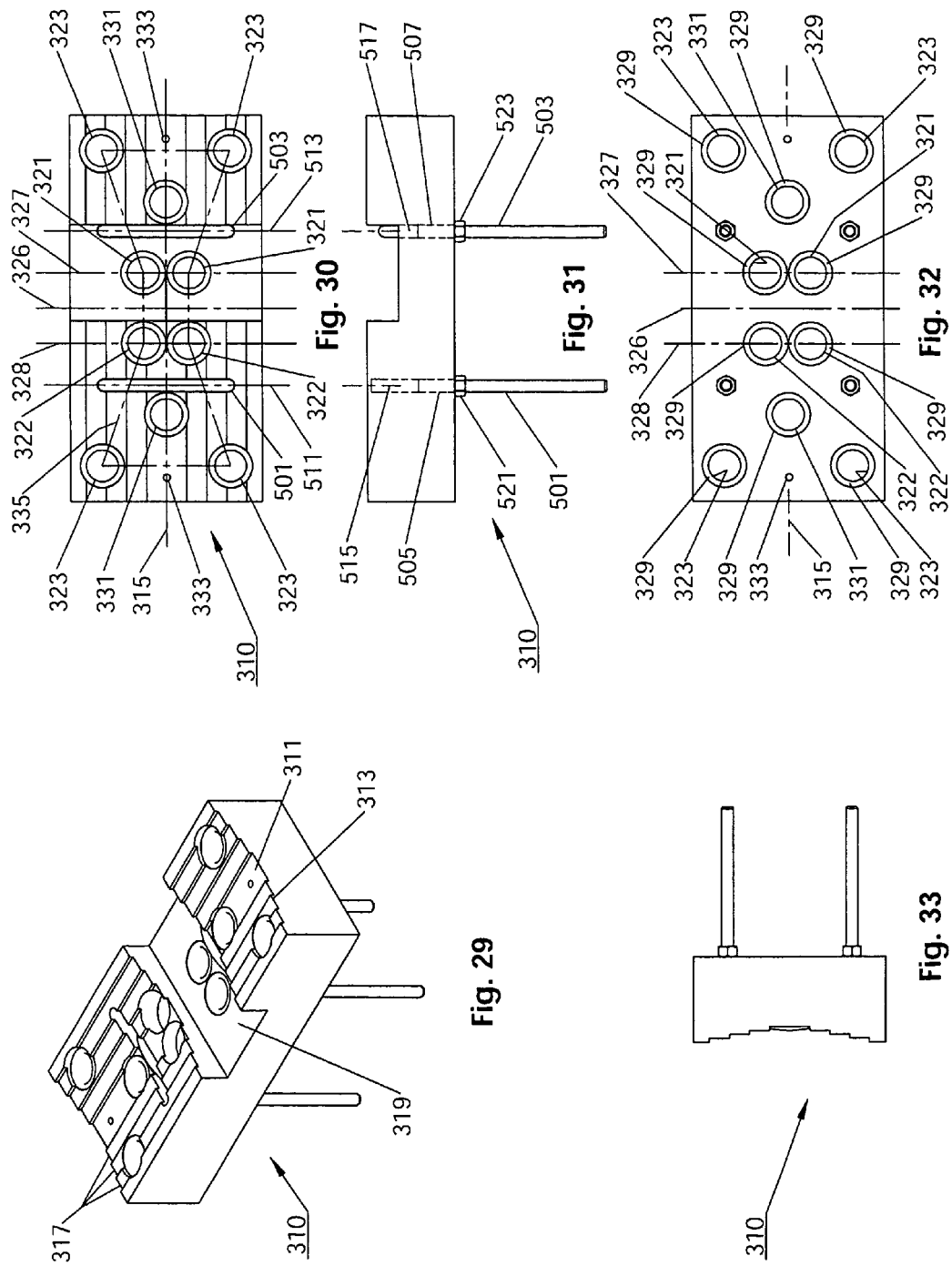

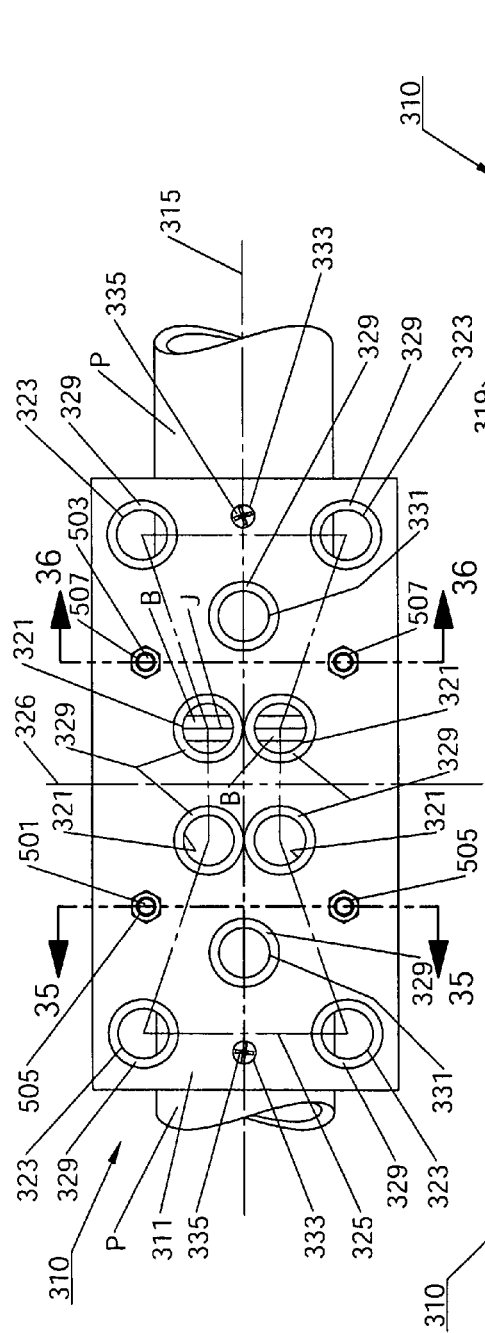
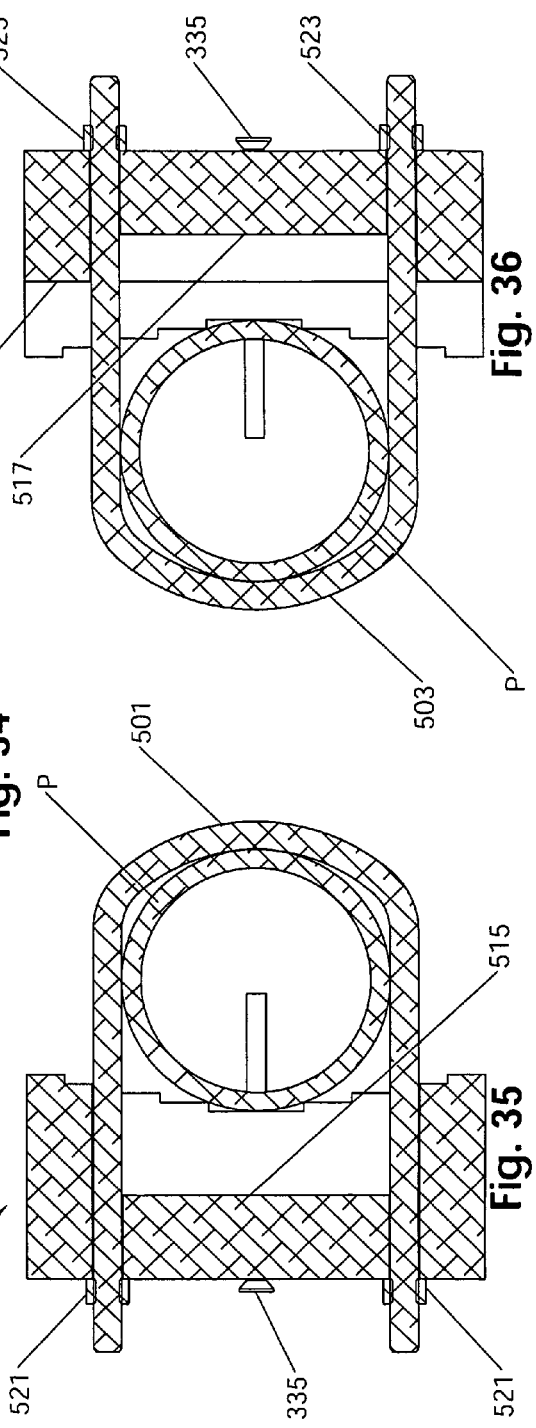

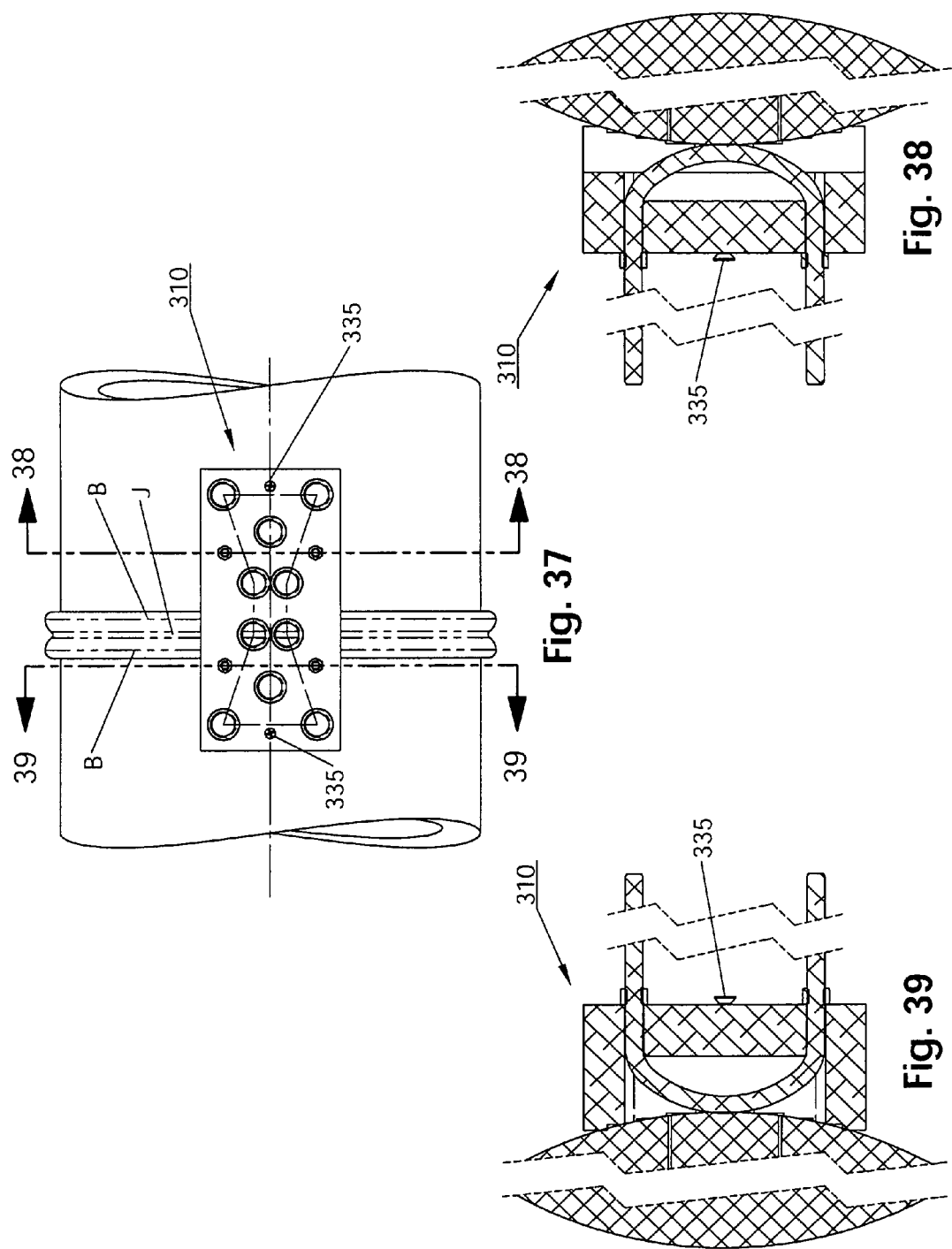

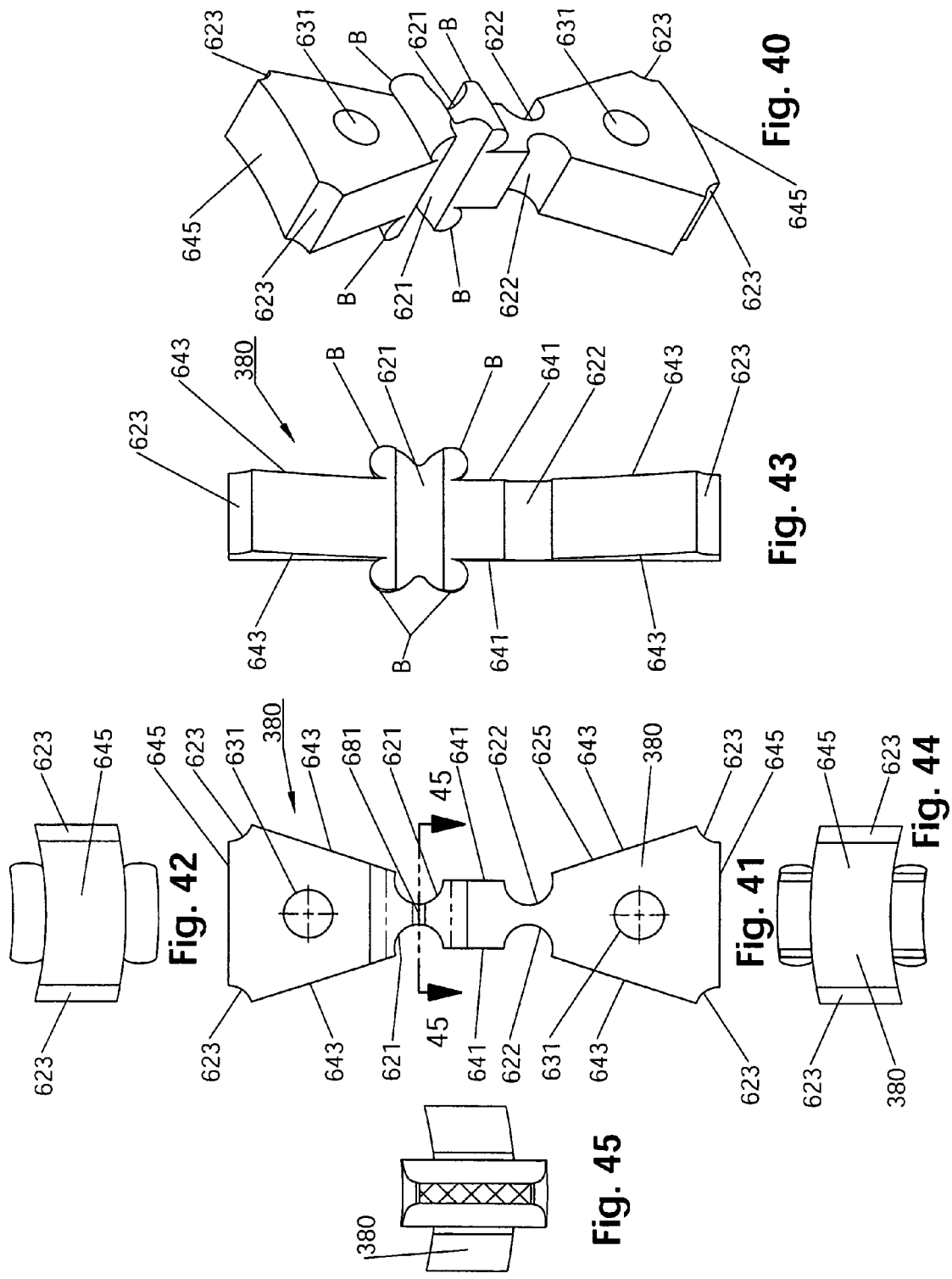

METHOD AND TEMPLATE FOR PRODUCING A TENSILE TEST COUPON

BACKGROUND OF THE INVENTION

This invention relates generally to the quality testing of heat-fused plastic pipe joints and more particularly concerns a method and template for producing a coupon which can be used to test the properties, such as the tensile strength and ductility, of a pipe joint as the pipe is being laid in the field.

Plastic pipes, such as pipes made of medium or high density polyethylene, can be joined by a variety of methods, a common joining method being butt-fusion. The procedure for this method involves inserting pipes to be fused into a specially designed fusion machine which aligns and holds the pipes axially with respect to each other and with pipe ends adjacent to each other, clamping the pipes securely in the jaws of the fusion machine, cleaning of the pipe ends to be fused, facing the pipe ends to ensure clean and square pipe ends with material exposed that is suitable for heat fusion, heating the pipe ends for an appropriate amount of time, and then joining the heated pipe ends under pressure and allowing the fused pipes to cool.

The integrity and usefulness of a pipeline requires quality fused joints with acceptable mechanical performance qualities. Therefore, tensile test methods have been devised which are intended to assure that a pipeline is being constructed of such quality as can reasonably be expected to pass final testing of the pipeline for use as designed. Unfortunately, most of the tensile test methods now available require instrumentation and apparatus which are not suited for field use. Therefore, tensile test coupons are used in laboratory test methods and are typically produced on non-portable machine tools.

A few destructive field-testing methods have been devised for checking the mechanical performance of the fused joint during pipeline production. The most common in-production test method is the "bend back" test. In the "bend back" test, a strap of material is extracted from a fused joint and its adjacent sections of pipe. The extracted strap is bent in such a direction that the maximum tensile and compressive bending stresses are applied to the portions of the strap that originated on the outer and inner diameters of the pipe. According to this test, a "good" joint is one which shows good bond integrity after bending. The straps are typically air bent, if practical, but if more force is needed to bend the strap to the degree required, implements may be applied.

The required length of the "bend back" strap may vary and, for greater pipe wall thicknesses, the forces required to bend the strap become high, containment in the case of failure becomes more difficult and the method becomes safety and cost prohibitive. In addition, the levels of stress imposed upon the fused joint are heavily dependent on uncontrolled or unknown factors such as the bend radius and the types of tooling used to bend the strap. These variables result in uncertainty as to the significance of any passing grade resulting from this test. Furthermore, for larger pipe diameters which require longer straps of pipe for testing, the material cost for the strap of pipe required to apply an appropriate bend test load can be quite expensive.

It is, therefore, an object of this invention to provide a method and template which facilitate the efficient and precise extraction of high quality tensile test coupons from a fused joint. Another object of this invention is to provide a method and template which facilitate speedy field evaluation of the quality of a fusion joint. A further object of this invention is to provide a method and template which ensures that the failure of the coupon in the tensile test will occur at the joint. It is also an object of this invention to provide a method and template which produce tensile test results which are qualitatively comparable to both/either a sample made from the pipe material and/or against predetermined qualitative criteria for acceptability. Still another object of this invention is to provide a method and template which require extraction of less pipe material for destructive tests than the "bend back" test.

SUMMARY OF THE INVENTION

In accordance with the invention, a method is provided for producing a tensile test coupon from a plastic pipe. The method includes the step of drilling an array of holes through a wall of the pipe. The drilled array defines a straight-line-connectable point-to-point pattern for the coupon. The method also includes the step of making straight line cuts with a reciprocating saw. The cuts connect the array of holes in the pattern of the coupon, thus separating the coupon from the pipe.

The holes of the coupon-defining array are arranged symmetrically in relation to a pair of intersecting axes, one axis being tangential to and the other axis being longitudinal along, an outer surface of the pipe. Preferably, the holes of the coupon-defining array define a bow-tie-like coupon symmetrical with respect to the tangential and longitudinal axes and the tangential axis lies in the plane of the interface between the fused sections of the pipe.

The method may also include the step of laying a template on the outer surface of the pipe. An array of holes through the template defines the straight-line-connectable point-to-point pattern for the coupon. With the template so positioned on the pipe, in the next step the template holes are used to guide the drilling of the array of pattern holes through the pipe. Thereafter, the method includes the step of removing the template from the pipe before making the straight line cuts.

The method may also include the additional step of drilling at least two more additional holes through the wall of the pipe and within the pattern of the coupon before cutting the coupon. These additional holes are oriented to facilitate application of tensile force to the extracted coupon along the narrowest cross-section of the coupon.

The template for use in producing a tensile test coupon from a plastic pipe has a plate contoured for stable abutment on the outer surface of the pipe. For example, the contour may be a V-groove aligning the longitudinal axis of the plate with the longitudinal axis of the pipe. An array of holes through the plate defines a straight-line-connectable point-to-point pattern for the coupon. At least two additional holes through the plate and within the pattern of the coupon are oriented to facilitate application of test tensile force to the extracted coupon at the narrowest cross-section of the coupon. The holes of the coupon-defining array may be arranged for symmetrical orientation in relation to a pair of intersecting axes, one axis being tangential to and the other axis being longitudinal along, the outer surface of the pipe when the plate is in stable abutment on the pipe. The symmetrical orientation of the array enables production of a symmetrical coupon. The at least two additional holes may be arranged for symmetrical orientation straddling the tangential axis and along the longitudinal axis. The symmetrical orientation of these holes, in cooperation with the symmetry of the coupon, allows the test tensile force to be symmetrically applied to the coupon. The plate is provided with a relief to receive beads formed on the outer surface of the pipe by fusion of the pipe along its plane of fusion interface. The tangential axis lies in the plane of interface so the plate can be in stable abutment on the pipe even though the outer diameter of the joint at the beads is greater than the outer diameter of the pipe. The holes of the coupon-defining array and the additional symmetrical holes may each be fitted with a hardened drill bushing.

Any of the above methods may further preferably include the step of securing the template to the outer surface of the pipe before drilling. For example, if at least two additional holes are provided through the template, the step of securing may be accomplished by driving screws which are inserted through the additional holes into the pipe.

In a second embodiment, a U-bolt securable template produces a symmetric tensile strength coupon. The template has a plate contoured for stable abutment against the outer surface of the pipe. Preferably, the contour is a step-tapered V-groove aligning the longitudinal axis of the plate with the longitudinal axis of the pipe.

An array of holes through the plate defines a straight-line-connectable bow-tie-like pattern for the coupon. The holes of the coupon-defining array may be arranged symmetrically in relation to a pair of intersecting axes, one of which will be tangential to and the other of which will be longitudinal along the outer surface of the pipe when the plate is in stable abutment against the pipe. The symmetrical orientation of the array enables production of a symmetrical coupon. The bow-tie-knot portion of coupon pattern may be defined by two or four of the holes of the array.

At least two additional holes oriented within the pattern of the coupon and extending through the plate facilitate the locating of sites on the coupon at which tensile force can be applied to the coupon at the narrowest cross-section of the bow-tie-knot portion of the pattern. The additional holes may be symmetrically displaced from the tangential axis and lie on the longitudinal axis. The symmetrical orientation of these holes, in cooperation with the symmetry of the coupon, allows the test tensile force to be symmetrically applied to the coupon.

The template can be secured to the pipe by use of two pairs of holes through the plate. Preferably, each pair lies outside of and straddles the pattern and the pairs are oriented to receive U-bolts to facilitate clamping the plate contour against the pipe. Alternatively, the template can be secured to the pipe by use of holes through the plate, preferably one pair of holes outside of and on lengthwise opposite ends of the pattern and receiving screws holding the plate contour against the pipe. The template can be provided with holes allowing use of both U-bolts and screws.

The plate is provided with a relief to receive beads formed by the fusion process on the outer surface of the pipe along its plane of fusion interface. The tangential axis lies in the plane of interface so the plate can be in stable abutment on the pipe even though the outer diameter of the joint at the beads is greater than the outer diameter of the pipe.

In a third embodiment, a template securable to a pipe by either screws or U-bolts produces an asymmetric tensile strength coupon. If the template has two tensile force holes straddling a four hole bow-tie-knot and is to be screwed to the pipe, the four bow-tie-knot holes are preferably aligned two on each side of the tangential axis with the relief aligned with two of the four holes on one side of the tangential axis. If the template has two tensile force holes straddling a four hole bow-tie-knot and is to be secured to the pipe with U-bolts, the four bow-tie-knot holes are preferably aligned two on each side of the tangential axis with the relief aligned with two of the four holes on one side of the tangential axis and the plate will have recesses for containing the cross-portions of the U-bolts when the bolts are fully inserted into their respective pairs of holes.

The method used in conjunction with the second and third embodiments includes the step of drilling an array of holes through a wall of the pipe. The drilled array defines a straight-line-connectable point-to-point pattern for the coupon. The method also includes the step of making straight line cuts with a reciprocating saw. The cuts connect the array of holes in the pattern of the coupon, thus separating the coupon from the pipe.

The holes of the coupon-defining array are arranged symmetrically in relation to a pair of intersecting axes, one axis being tangential to and the other axis being longitudinal along an outer surface of the pipe. Preferably, the holes of the coupon-defining array define a bow-tie-like coupon symmetrical with respect to the tangential and longitudinal axes and the tangential axis lies in the plane of the interface between the fused sections of the pipe.

The method may be facilitated by the step of laying a template on the outer surface of the pipe. The template defines the locations of the array of holes of the straight-line-connectable point-to-point pattern for the coupon. With the template so positioned on the pipe, the template holes are used to guide the drilling of the array of pattern holes through the pipe. After drilling the array of pattern holes, the method includes the step of removing the template from the pipe before making the straight line cuts.

The method may also include the additional step of drilling at least two more additional holes through the wall of the pipe and within the pattern of the coupon before cutting the coupon. These additional holes are oriented to facilitate application of tensile force to the extracted coupon along the narrowest cross-section of the coupon. In this case, if the method is facilitated by use of a template, the template will also define the locations of the tensile force holes to guide the drilling of the tensile force holes through the pipe before removing the template from the pipe.

The method may further preferably include the step of securing the template to the outer surface of the pipe before drilling by use of screws or U-bolts.

BRIEF DESCRIPTION OF THE DRAWINGS

Other objects and advantages of the invention will become apparent upon reading the following detailed description and upon reference to the drawings in which:

FIG. 3 is a side elevation view of the tensile test coupon template of FIG. 1;

FIG. 4 is a plan view of the top of the tensile test coupon template of FIG. 1;

FIG. 5 is an end view of the tensile test coupon template of FIG. 1;

FIG. 6 is an end view of the tensile test coupon template of FIG. 1 mounted on a pipe;

FIG. 7 is cross-sectional view taken along the line 7-7 of FIG. 6;

FIG. 8 is a side elevation view of the tensile test coupon template of FIG. 1 mounted on a pipe;

FIG. 9 is a plan view of the top of the tensile test coupon template of FIG. 1 mounted on a pipe;

FIG. 10 is a perspective view illustrating a step of the method of using the tensile test coupon template of FIG. 1;

FIG. 11 is a perspective view illustrating another step of the method of using the tensile test coupon template of FIG. 1;

FIG. 12 is a perspective view illustrating yet another step of the method of using the tensile test coupon template of FIG. 1;

FIG. 18 is a perspective view of a second embodiment of the tensile test coupon template;

FIG. 19 is a plan view of the bottom of the template of FIG. 18;

FIG. 20 is a side elevation view of the tensile test coupon template of FIG. 18;

FIG. 21 is a plan view of the top of the tensile test coupon template of FIG. 18;

FIG. 22 is an end view of the tensile test coupon template of FIG. 18;

FIG. 23 is a plan view of the top of the tensile test coupon template of FIG. 18 mounted on a smaller diameter pipe;

FIG. 24 is a cross-sectional view taken along the line 24-24 of FIG. 23;

FIG. 25 is a cross-sectional view taken along the line 25-25 of FIG. 23;

FIG. 26 is a plan view of the top of the tensile test coupon template of FIG. 18 mounted on a larger diameter pipe;

FIG. 27 is a cross-sectional view taken along the line 27-27 of FIG. 26;

FIG. 28 is a cross-sectional view taken along the line 28-28 of FIG. 26;

FIG. 29 is a perspective view of a third embodiment of the tensile test coupon template;

FIG. 30 is a plan view of the bottom of the template of FIG. 29;

FIG. 31 is a side elevation view of the tensile test coupon template of FIG. 29;

FIG. 32 is a plan view of the top of the tensile test coupon template of FIG. 29;

FIG. 33 is an end view of the tensile test coupon template of FIG. 29;

FIG. 34 is a plan view of the top of the tensile test coupon template of FIG. 29 mounted on a smaller diameter pipe;

FIG. 35 is a cross-sectional view taken along the line 35-35 of FIG. 34;

FIG. 36 is a cross-sectional view taken along the line 36-36 of FIG. 34;

FIG. 37 is a plan view of the top of the tensile test coupon template of FIG. 29 mounted on a larger diameter pipe;

FIG. 38 is a cross-sectional view taken along the line 38-38 of FIG. 37;

FIG. 39 is a cross-sectional view taken along the line 39-39 of FIG. 37;

FIG. 40 is a perspective view of an asymmetric tensile test coupon derived from a pipe joint by the method of the present invention;

FIG. 41 is a top plan view of the coupon of FIG. 40;

FIG. 42 is an end view of the coupon of FIG. 40;

FIG. 43 is a side elevation view of the coupon of FIG. 40;

FIG. 44 is an end view of the coupon of FIG. 40; and

FIG. 45 is cross-sectional view taken along the line 45-45 of FIG. 40.

Figure 1:
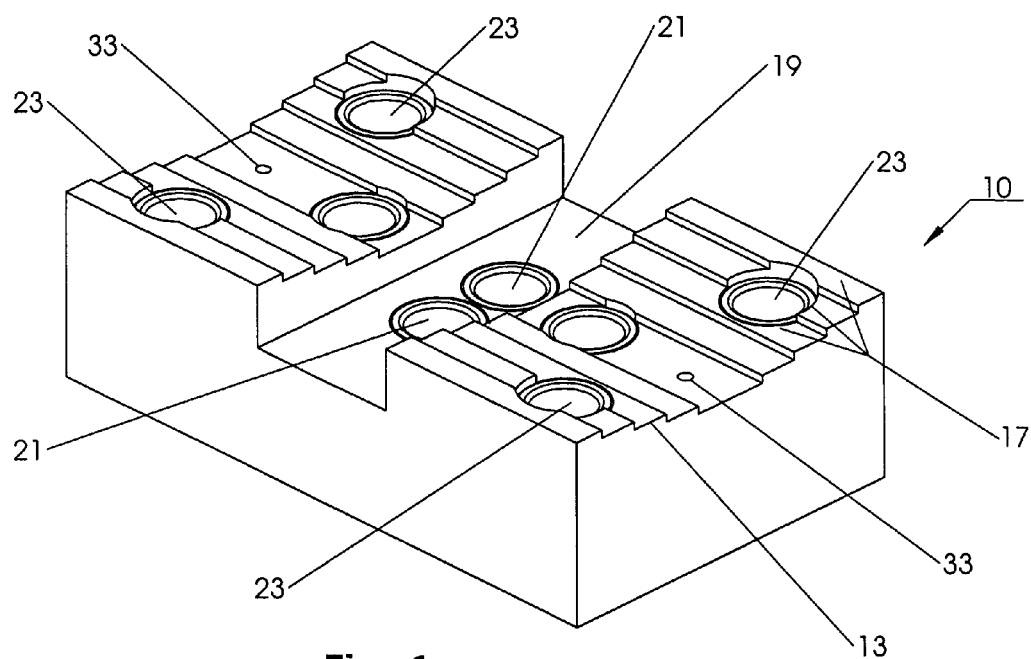
FIG. 1 is a perspective view of a first embodiment of the tensile test coupon template.
Figure 2:
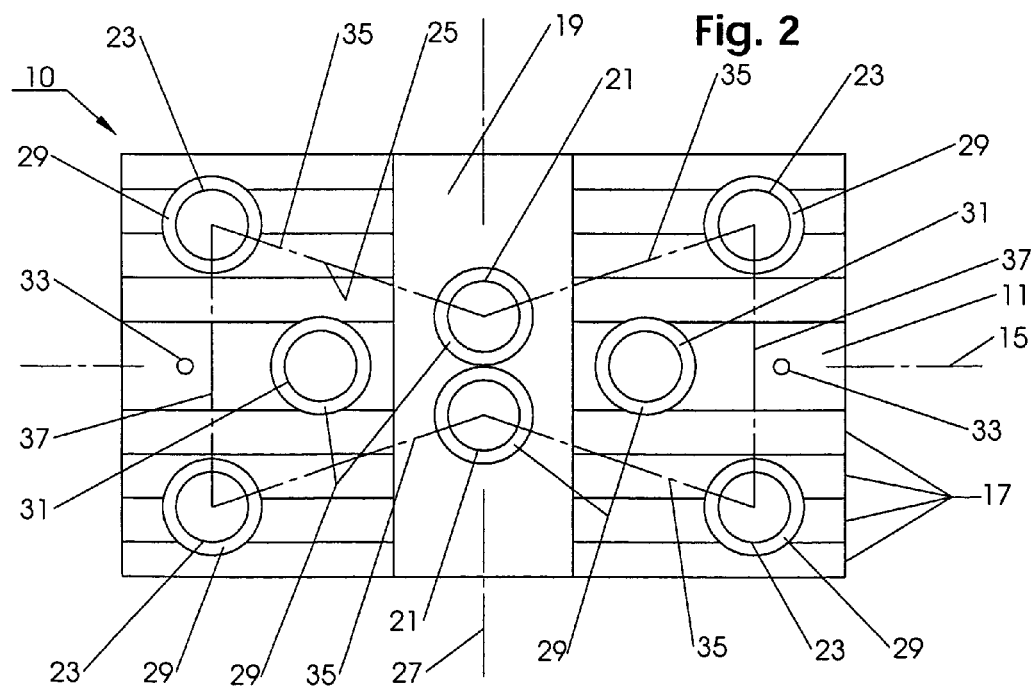
FIG. 2 is a plan view of the bottom of the template of FIG. 1.
Figure 14:
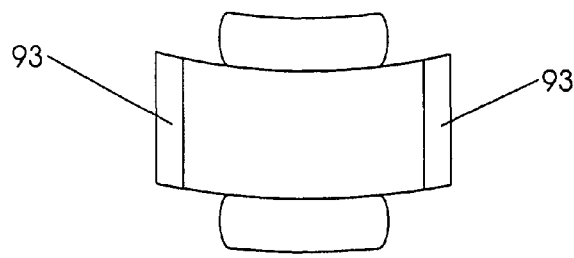
FIG. 14 is an end view of the coupon of FIG. 13.

While the invention will be described in connection with preferred embodiments thereof, it will be understood that it is not intended to limit the invention to those embodiments or to the details of the construction or arrangement of parts illustrated in the accompanying drawings.

DETAILED DESCRIPTION

First Embodiment of the Template

Turning to FIGS. 1-12, a screw-in-place, symmetric mount embodiment of a template 10 for producing a tensile test coupon 80, seen in FIGS. 13-17, from a plastic pipe P or a fused joint J of a plastic pipe P is illustrated. The template 10 is useful over a broad range of pipe diameters and compositions, but is particularly applicable for medium or high density polyethylene pipes.

The template 10 is formed using a relatively thick plate of material such as commercially available aluminum or steel suited for machining. The template 10 has a base 11 which, in using the template 10, will be abutted against the outer surface of the pipe P. The contour of the base 11 can take many shapes so long as the template 10 is stable in its alignment when held against a pipe P.

As shown, the base 11 has a V-groove 13 which, in cross-section, is transverse to the longitudinal axis 15 of the template 10. Thus, the pipe and template longitudinal axes L and 15 will be parallel when the template 10 is abutted in its stable condition against the pipe P. As shown, the V-groove 13 has a stepped pipe-contacting surface 17 which allows the template 10 to center on the curvature of the pipe P. The steps 17 can be configured to further stabilize the template 10 on the pipe P by reason of their gripping effect or to allow use of the same template 10 with pipes P of different diameters.

A relief 19 in the base 11 extends perpendicular to the longitudinal axis 15 of the template 10. The relief 19 allows the template 10 to be centered over the beads B of a fusion joint J but does not prevent attachment of the template 10 anywhere along the pipe P regardless of the presence of a fusion joint J.

The template 10 has an array of holes 21 and 23 through it which define a pattern 25 in the template 10 in the desired shape of the tensile test coupon 80. These holes 21 and 23 are starting and ending points for saw cuts by a reciprocating saw. As shown, the holes 21 and 23 are arrayed to define a straight-line-connectable point-to-point pattern 25, considering the center of each hole 21 and 23 as the point of definition. The pattern 25 shown has a bow-tie-like shape which is symmetric in relation to the longitudinal 15 and relief 27 axes of the template 10. As shown, four holes 23 of the array allow the operator to form the outer "corners" of the coupon 80 and two holes 21 of the array allow the operator to connect the "corners" to the narrowest cross-section 81 of the bow-tie-like coupon 80. As shown, the narrowest-cross-section holes 21 are aligned at the center of the bow-tie-like pattern. As shown, each hole 21 and 23 of the array is fitted with a hardened drill bushing 29 which will precisely guide a drill bit driven by a hand drill. The drill bushings 29 ensure that the holes 21 and 23 produced during drilling will be parallel to each other to a close degree of precision and reduce wear on the template 10.

Additional holes 31, as shown two holes 31 with the same diameters as the holes 21 and 23 of the coupon array, extend through the template 10 within the confines of the pattern 25. The additional holes 31 will be used in a pin and clevis arrangement associated with a tensile testing device for application of tensile force to the coupon 80. In the two additional hole configuration shown, the holes 31 are centered on the longitudinal axis 15 of the pattern and symmetrically straddle the relief axis 27 so that the tensile force will be evenly applied at the narrow cross-section 81 of the coupon 80. As shown, the additional holes 31 are also each fitted with a hardened drill bushing 29.

In use, it is preferred that the template 10 be temporarily affixed to the pipe P. As shown, this is accomplished by use of mounting holes 33, as shown two holes 33 which extend through the template 10, symmetrically straddling the relief 19 and aligned on the longitudinal centerline 15 of the template 10. Coarsely threaded wood screws can be driven through the holes 33 into the pipe P to temporarily secure the template 10 in place. As shown, the mounting holes 33 are outside of the confines of the coupon pattern 25. However, the exact placement and number of the mounting holes 33 is not critical. The holes 33 need only serve as pilot holes for the wood screws which are driven into the pipe P to hold the template 10 firmly against the pipe P and anchor the template 10 while the coupon pattern 21 and 23 and tensile force 31 holes are drilled.

Second Embodiment of the Template

The first embodiment template 10 used screws to fix the template securely to the outer surface of the pipe to be tested. This method works well where pipes are fairly structurally stable, as when pipes are heavy wall and/or of large diameter. This method works adequately to stabilize the template to the degree necessary to produce a precisely drilled coupon. Smaller pipes lack the necessary rigidity and tend to displace out of the way of the drill bit as the holes are being drilled, possibly leading to distorted hole arrays in the coupons so that the drilled holes are not precisely aligned as is desired. The U-bolt arrangement envelopes the pipe being tested and draws it into firm contact with the stabilizing contour of the template. The U-bolts are threaded on their ends and threaded nuts are used to tighten them against the pipe, drawing it into firm contact with the template. These U-bolts also help the pipe to maintain its shape while it is being drilled.

Looking at FIGS. 18-28, a U-bolt, symmetric mount embodiment of the template 210 for producing a tensile test coupon 80, best seen in FIGS. 13-17, from a plastic pipe P or a fused joint J of a plastic pipe P is illustrated. The template 210 is useful over a broad range of pipe diameters and compositions, but is particularly applicable for smaller diameter medium or high density polyethylene pipes.

The template 210 is formed using a relatively thick plate of material such as commercially available aluminum or steel suited for machining. The template 210 has a base 211 which, in using the template 210, will be abutted against the outer surface of the pipe P. The contour of the base 211 can take many shapes so long as the template 210 is stable in its alignment when held against a pipe P.

As shown, the base 211 has a V-groove 213 which, in cross-section, is transverse to the longitudinal axis 215 of the template 210. Thus, the pipe and template longitudinal axes L and 215 will be parallel when the template 210 is abutted in its stable condition against the pipe P. As shown, the V-groove 213 has a stepped pipe-contacting surface 217 which allows the template 210 to center on the curvature of the pipe P. The steps 217 can be configured to further stabilize the template 210 on the pipe P by reason of their gripping effect or to allow use of the same template 210 with pipes P of different diameters.

A relief 219 in the base 211 extends perpendicular to the longitudinal axis 215 of the template 210. As best seen in FIGS. 23 and 26, the relief 219 allows the template 210 to be centered over the beads B of a fusion joint J but does not prevent attachment of the template 210 anywhere along the pipe P regardless of the presence of a fusion joint J.

Looking again at FIGS. 18-22, the template 210 has an array of holes 221 and 223 through it which define a pattern 225 in the template 210 in the desired shape of the tensile test coupon 80, best seen in FIGS. 13-17. These holes 221 and 223 are starting and ending points for saw cuts by a reciprocating saw. As shown, the holes 221 and 223 are arrayed to define a straight-line-connectable point-to-point pattern 225, considering the center of each hole 221 and 223 as the point of definition. The pattern 225 shown has a bow-tie-like shape which is symmetric in relation to the longitudinal 215 and relief 227 axes of the template 210. As shown, four holes 223 of the array allow the operator to form the outer "corners" of the coupon 80 and two holes 221 of the array allow the operator to connect the "corners" to the narrowest cross-section of the pattern 225 to form the bow-tie-like shape of the coupon 80. As best seen in FIG. 19, the narrowest-cross-section holes 221 are aligned on the relief axis 227 which is perpendicular to the longitudinal axis 215 and will be tangential to the pipe P and which is at the center of the bow-tie-like pattern 225. As shown, each hole 221 and 223 of the array is fitted with a hardened drill bushing 229 which will precisely guide a drill bit driven by a hand drill. The drill bushings 229 ensure that the holes 221 and 223 produced during drilling will be parallel to each other to a close degree of precision and reduce wear on the template 210.

Figures 13, 15, 17:
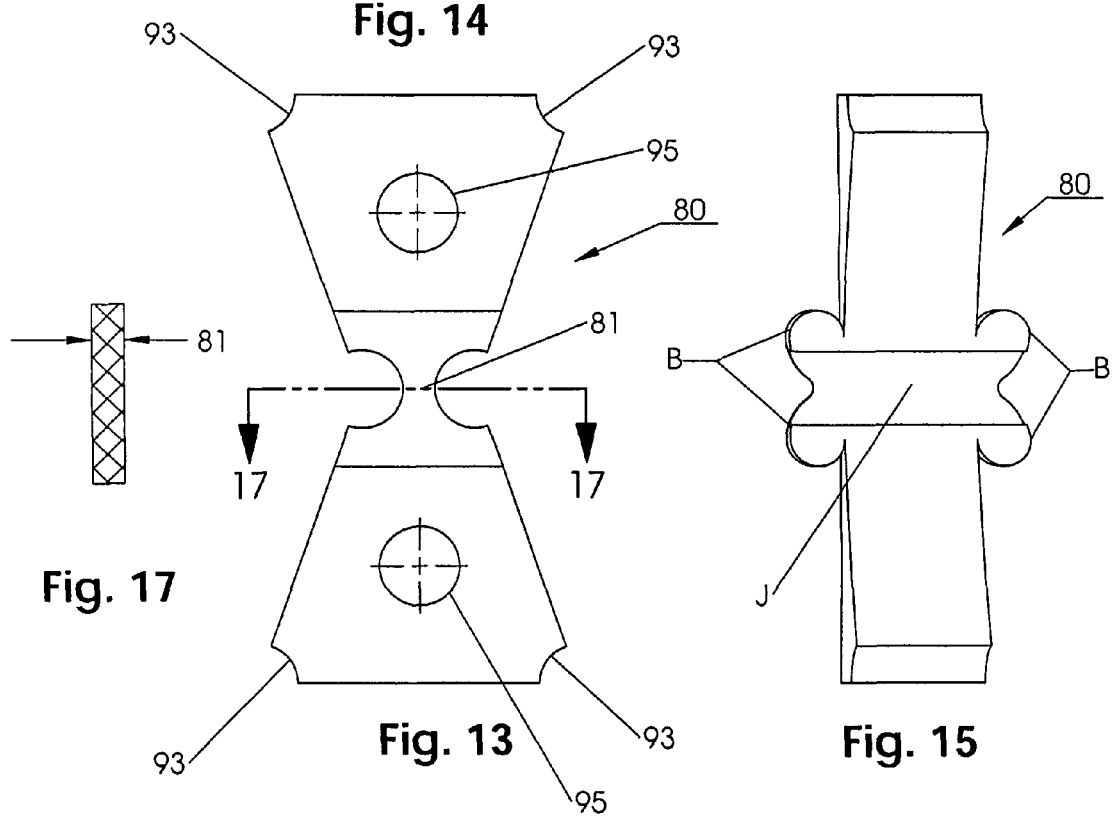
FIG. 13 is a top plan view of a symmetric tensile test coupon derived from a pipe joint by the method of the present invention.
FIG. 15 is a side elevation view of the coupon of FIG. 13.
FIG. 17 is cross-sectional view taken along the line 17-17 of FIG. 13.
Figure 16:
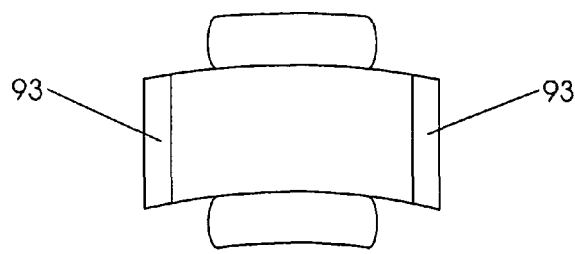
FIG. 16 is another end view of the coupon of FIG. 13.

Additional holes 231, as shown two holes 231 with the same diameters as the holes 221 and 223 of the coupon array, extend through the template 210 within the confines of the pattern 225. The additional holes 231 will be used in a pin and clevis arrangement associated with a tensile testing device for application of tensile force to the coupon 80 formed by use of the template 210. In the two additional hole configuration shown in FIG. 19, the holes 231 are centered on the longitudinal axis 215 of the pattern and symmetrically straddle the relief axis 227 so that the tensile force will be evenly applied at the narrow cross-section 81 of the coupon 80, as seen in FIG. 13. As shown, the additional holes 231 are also each fitted with a hardened drill bushing 229.

Looking at FIGS. 23-25, it is preferred that, when used with smaller diameter pipes, the template 210 be temporarily affixed to the pipe P using a pair of U-bolts 401 and 403. Two pairs of holes 405 and 407 are provided through the plate. Each pair 405 and 407 lies outside of and straddles the pattern 225. The pairs of holes 405 and 407 are oriented to receive the U-bolts 401 and 403 to secure the contour of the base 211 of the plate against the pipe P. As shown, the pattern 225 formed by the array of holes 221 and 223 is symmetrical in relation to the intersecting tangential and longitudinal axes 227 and 215. The two additional holes 231 are symmetrically displaced from the tangential axis 227 and lie on the longitudinal axis 215. Each pair of U-bolt holes 405 and 407 symmetrically straddles the longitudinal axis 215 and lies on axes 411 and 413 which are parallel to the tangential axis 227. As shown, each pair of holes 405 and 407 is within the relief 219 and is symmetrically displaced from the tangential axis 227. The relief 219 has recesses 415 and 417 for containing cross-portions of the U-bolts 401 and 403 when the bolts 401 and 403 are fully inserted into their respective pairs of holes 405 and 407.

As best seen in FIGS. 24 and 25, when this symmetric embodiment of the template 210 is used with smaller pipes P, the symmetry permits the template 210 to be firmly secured to the pipe P by tightening pairs of nuts 421 and 423 on their respective U-bolts 401 and 403. In addition, two holes 233 can be provided through the template 210 which symmetrically straddle the relief 219 and align on the longitudinal centerline 215 of the template 210. Coarsely threaded wood screws 235 can be driven through the holes 233 into the pipe P to further secure the template 210 in place. As shown, the mounting holes 233 are outside of the confines of the coupon pattern 225. However, the exact placement and number of the mounting holes 233 is not critical. The holes 233 need only serve as pilot holes for the wood screws 235 which are driven into the pipe P to hold the template 210 firmly against the pipe P and anchor the template 210 while the coupon pattern holes 221 and 223 and tensile force holes 231 are drilled.

Looking at FIGS. 26-28, it is preferred that, when used with larger diameter pipes, the template 210 be temporarily affixed to the pipe P using only the coarsely threaded wood screws 235. As best seen in FIGS. 27 and 28, if the U-bolts 401 and 403 are not used to secure the template 210 to the pipe P, the pairs of nuts 421 and 423 are tightened to secure the U-bolts 421 and 423 to the template 210 with the cross-portions of the bolts 401 and 403 seated in the recesses 415 and 417 of the relief 219. The depth of the recesses 415 and 417 is sufficient to afford clearance for the cross-portions of the bolts 401 and 403 when the pipe P is fully seated against the contour of the base 211 of the template 210.

Method for Producing Symmetric Coupons

The method for producing a tensile test coupon 80 from a plastic pipe P involves the steps of drilling an array of holes 21 and 23 through the wall of the pipe P to define a straight-line-connectable point-to-point pattern 25 for the coupon 80, drilling at least two additional holes 31 through the wall of the pipe P within the pattern 25 of the coupon 80 for facilitating application of tensile force to the coupon 80 at its narrowest cross-section 81 and making straight line cuts 35 and 37 with a reciprocating saw, the cuts 35 and 37 connecting the array of holes 21 and 23 in the pattern 25 of the coupon 80 to separate the coupon 80 from the pipe P.

Looking at FIGS. 11-17 and using the first embodiment template 10 of FIGS. 1-10, the method can be applied with speed and accuracy in the field. At the geographic location of the fusion process, the method involves the steps of laying the template 10 on the outer surface of the pipe P, using the template holes 21, 23 and 31 to guide the drilling of an array of coupon holes 91, 93 and additional holes 95 through the pipe P and removing the template 10 from the pipe P before making the cuts 35 and 37 to connect the pattern holes 91 and 93 in the coupon 80. Before drilling, the template 10 can be secured to the outer surface of the pipe P, as by driving screws through the template mounting holes 33.

Looking at FIGS. 11-17 and 23-28 and using the second embodiment template 10 of FIGS. 18-22, the method can be applied with speed and accuracy in the field. At the geographic location of the fusion process, the method involves the steps of laying the template 210 on the outer surface of the pipe P, using the template holes 221, 223 and 231 to guide the drilling of an array of coupon holes 91, 93 and additional holes 95 through the pipe P and removing the template 210 from the pipe P before making the cuts 35 and 37 to connect the pattern holes 91 and 93 in the coupon 80. Before drilling, the template 210 can be secured to the outer surface of the pipe P, as by using U-bolts 401 and 403 inserted through the pairs of template bolt holes 405 and 407 and secured with nuts 421 and 423.

In the laying step, the V-groove 13 aligns the template 10 or 210 and pipe longitudinal axes L and 15 or 215, if the coupon 80 is to be taken at a fusion joint J of the pipe P, the template holes 21 or 221 at the narrowest cross-section 81 of the coupon 80 are visually aligned on the plane of the fusion interface between the fusion beads B which lie in the relief 19 or 219 on the template 10 or 210. In the securing step, a screwdriver can be used to install coarsely threaded wood screws through the mounting holes 33 or 233 of the template 10 or 210 into the pipe P to be tested. The screws firmly, but temporarily, attach the template 10 or 210 to the outer surface of the pipe P. A hand drill with a bit of appropriate diameter to accommodate the width of a reciprocating saw blade is used to drill the coupon pattern 21 and 23 or 221 and 223 and tensile force 31 or 231 holes. A twist drill bit of diameter and length of flute to evacuate the drilled pipe chips and shavings out the upper side of the template 10 or 210 when fully engaged with the pipe P is preferred for drilling through the holes 21, 23 and 31 or 221, 223 and 231 and the pipe P. The template 10 or 210 guides the bit through the hardened drill bushings and into and through the wall of the pipe P. The screwdriver is again used to unthread the wood screws from the pipe P and remove the template 10 or 210. A hand held reciprocating saw can be used to make cuts 35 and 37 which connect the outer or coupon pattern holes 91 and 93 in the pipe P, leaving the pin and clevis holes 95 within the confines of the coupon 80 intact and separating the coupon 80 to be tested from the pipe P. Preferably, the saw cuts 35 are made in the pipe P from the center holes 91 to the corner holes 93 and then two final cuts 37 are made from corner hole 93 to corner hole 93 parallel to the plane of fusion between the beads B, the final cuts 37 freeing the coupon 80 from the pipe P. The coupon 80 is ready to be loaded into an on-site tensile testing device such as a manually pumped, hydraulically actuated tensile testing machine, suitable for field use by a single operator. The operator then removes the coupon 80 from the tensile testing apparatus and inspects the surfaces of failure, making a determination of the quality of the joint J on the basis of comparison to a base pipe failure prepared using the same template 10 or 210 and method, or on the basis of other pre-determined criteria. Thus, using the tools above described, the entire test process can be accomplished on-site by a single operator.

The template 10 or 210 and method allow efficient and precise extraction of a number of high quality tensile coupons 80 from a pipe P or from the fused joint J of a pipe P. The coupons 80 are tested to failure in a field-suitable, well controlled, self contained, tensile testing apparatus for a speedy field evaluation of the quality of the fusion joint J. The narrowing bow-tie-like pattern of the coupon 80 ensures that the failure of the coupon 80 in the tensile test will occur at the narrowest section 81 of the coupon 80. If a joint J is being tested, the narrowest cross-section 81 can be visually aligned with the joint J to ensure that it is the joint J that will be tested.

The results of the tensile test can be qualitatively compared to a sample made from the base pipe material and/or evaluated against predetermined qualitative criteria for acceptability. These qualitative criteria may be established by correlation with laboratory type tensile testing or on other reasonable bases. Such qualitative testing is not possible with known in-field destructive tests.

The material consumed by this destructive test is reasonably approximated by the length of the template 10 or 210 so, in many cases, substantially less material is consumed than in known destructive tests such as the "bend back" test.

The relief 19 or 219 of the template 10 or 210 straddles the beads B of excess molten material which was pushed out of the joint interface during the joining operation of the fusion procedure so that the narrowest cross-section of the coupon pattern 25 or 225 in the template 10 or 210 may be aligned carefully with the plane of the fusion. This ensures that the narrowest cross-section 81 of the coupon 80 is in the fused region of the pipe P.

This method and template 10 or 210 for field-testing provides quick and definitive qualitative results without imposing burdensome costs in time or material upon the operator.

Third Embodiment of the Template

Looking at FIGS. 29-33, a U-bolt, asymmetric mount embodiment of the template 310 for producing a tensile test coupon 380, best seen in FIGS. 40-45, from a plastic-pipe P or a fused joint J of a plastic pipe P is illustrated. The template 310 is useful over a broad range of pipe diameters and compositions, but is particularly applicable for smaller diameter medium or high density polyethylene pipes.

A coupon hole-array profile with a single reduced section lying in the plane of the interface of two fused pipes has to be interpreted in order to provide a meaningful estimation as to the quality of the joint. While a tensile coupon prepared from a single stick of good quality base pipe will always fail in the reduced area in a ductile fashion, a tensile coupon prepared at a pipe joint presents multiple possibilities. The very worst joints will break abruptly under tensile load, leaving a smooth parting face, and showing no evidence of cohesion between the pipe ends being fused. The very best joints will show a level of ductility prior to break roughly equivalent to the base pipe material. Most joints show behaviors between these extremes, so the user of the method must refer to criteria developed in advance in order to decide whether the performance of the particular fused joint is acceptable or not.

In order to make the comparison to the base pipe intrinsic to the design of the coupon, a modified coupon 380 provides for two in-line, reduced sections, possibly but not necessarily of the same width, with the tensile force application holes straddling these reduced sections. The stronger connection can be determined by applying a tensile load to them in series and then determining which cross section fails first. By adjusting the narrowest width of the base pipe cross section, that is the space between bow-tie-knot holes 622 which are aligned over the base pipe, the performance standard of the narrowest fused cross section 381 between the bow-tie-knot holes 621 which are aligned over the joint J can be varied. For example, if the base pipe cross section is 90% of the area of the fused joint cross section 381, and the failure happens in the base pipe, the joint J has a demonstrated strength of at least 90% of the base pipe adjacent to the joint J.

Thus, by varying the spacing between the coupon defining array holes, thereby adjusting the width of the reduced, or bow-tie-knot section, a numerical strength comparison can be designed into the tensile test coupon, without a need for even qualitative judgment.

The template 310 is formed using a relatively thick plate of material such as commercially available aluminum or steel suited for machining. The template 310 has a base 311 which, in using the template 310, will be abutted against the outer surface of the pipe P. The contour of the base 311 can take many shapes so long as the template 310 is stable in its alignment when held against a pipe P.

As shown, the base 311 has a V-groove 313 which, in cross-section, is transverse to the longitudinal axis 315 of the template 310. Thus, the pipe and template longitudinal axes L and 315 will be parallel when the template 310 is abutted in its stable condition against the pipe P. As shown, the V-groove 313 has a stepped pipe-contacting surface 317 which allows the template 310 to center on the curvature of the pipe P. The steps 317 can be configured to further stabilize the template 310 on the pipe P by reason of their gripping effect or to allow use of the same template 310 with pipes P of different diameters.

A relief 319 in the base 311 extends perpendicular to the longitudinal axis 315 of the template 310 and is centered on a tangential axis 327 which is offset from the center axis 326 of the template 310. As best seen in FIGS. 34 and 37, the offset relief 319 can be centered over the beads B of a fusion joint J but does not prevent attachment of the template 310 anywhere along the pipe P regardless of the presence of a fusion joint J.

Returning to FIGS. 29-33, the template 310 has an array of holes 321, 322 and 323 through it which define a pattern 325 in the template 310 in the desired shape of the tensile test coupon 380, best seen in FIGS. 40-45. These holes 321, 322 and 323 are starting and ending points for saw cuts by a reciprocating saw. As shown, the holes 321, 322 and 323 are arrayed to define a straight-line-connectable point-to-point pattern 325, considering the center of each hole 321, 322 and 323 as the point of definition. The pattern 325 shown has a bow-tie-like shape which is symmetric in relation to the longitudinal 315 and tangential axes 326 of the template 310 with the relief 319 offset in the pattern. As shown, four holes 323 of the array allow the operator to form the outer "corners" of the coupon 380 and four holes 321 and 322 of the array allow the operator to connect the "corners" to the narrowest cross-section of the pattern 325 to form the bow-tie-like shape of the coupon 380. As best seen in FIG. 30, two of the narrowest cross-section holes 321 are aligned on the center relief axis 327 which is perpendicular to the longitudinal axis 315 and will be tangential to the pipe P. The other two of the narrowest cross-section holes 322 are aligned on another axis 328 which is perpendicular to the longitudinal axis 315 and will be tangential to the pipe P. The latter holes 322 are not within the relief 319. As shown, each hole 321, 322 and 323 of the array is fitted with a hardened drill bushing 329 which will precisely guide a drill bit driven by a hand drill. The drill bushings 329 ensure that the holes 321, 322 and 323 produced during drilling will be parallel to each other to a close degree of precision and reduce wear on the template 310.

Additional holes 331, as shown two holes 331 with the same diameter as the holes 321, 322 and 323 of the coupon array, extend through the template 310 within the confines of the pattern 325. The additional holes 331 will be used in a pin and clevis arrangement associated with a tensile testing device for application of tensile force to the coupon 380, best seen in FIG. 40, formed by use of the template 310. In the additional hole configuration shown in FIGS. 29-33, the holes 331 are centered on the longitudinal axis 315 of the pattern and symmetrically straddle the center axis 326 of the bow-tie pattern 325 so that the tensile force will be evenly applied at the narrow cross-section 381 of the coupon 380. As shown, the additional holes 331 are also each fitted with a hardened drill bushing 329.

Looking at FIGS. 34-36, it is preferred that, when used with smaller diameter pipes, the template 310 be temporarily affixed to the pipe P using a pair of U-bolts 501 and 503. Two pairs of holes 505 and 507 are provided through the plate. Each pair 505 and 507 lies outside of and straddles the pattern 325. The pairs of holes 505 and 507 are oriented to receive the U-bolts 501 and 503 to secure the contour of the base 311 of the plate against the pipe P. As shown, the pattern 325 formed by the array of holes 321, 322 and 323 is symmetrical in relation to the intersecting tangential and longitudinal axes 326 and 315. The two additional holes 331 are symmetrically displaced from the tangential axis 326 and lie on the longitudinal axis 315. Each pair of U-bolt holes 505 and 507 symmetrically straddles the longitudinal axis 315 and lies on axes 511 and 513 which are parallel to the tangential axes 326, 327 and 328. As shown, one pair of holes 505 is outside of the relief 319 and the other pair of holes 507 is within the relief 319. The pairs of holes 505 and 507 are symmetrically displaced on opposite sides of the tangential axis 326. The one pair of holes 505 has an associated recess 515 in the contour 313 and the other pair of holes has an associated recess 517 in the relief 319. The recesses 515 and 517 have a depth sufficient to contain cross-portions of the U-bolts 501 and 503 when the bolts 501 and 503 are fully inserted into their respective pairs of holes 505 and 507.

As best seen in FIGS. 35 and 36, when this asymmetric embodiment of the template 310 is used with smaller pipes P, the template 310 can be firmly secured to the pipe P with the relief 319 over the pipe joint J by tightening pairs of nuts 521 and 523 on their respective U-bolts 501 and 503. In addition, two holes 333 can be provided through the template 310 which symmetrically straddle the center tangential axis 326 and align on the longitudinal centerline 315 of the template 310. Coarsely threaded wood screws 335 can be driven through the holes 333 into the pipe P to further secure the template 310 in place. As shown, the mounting holes 333 are outside of the confines of the coupon pattern 325. However, the exact placement and number of the mounting holes 333 is not critical. The holes 333 need only serve as pilot holes for the wood screws 335 which are driven into the pipe P to hold the template 310 firmly against the pipe P and anchor the template 310 while the coupon pattern holes 321, 322 and 323 and tensile force holes 331 are drilled.

Looking at FIGS. 37-39, it is preferred that, when used with larger diameter pipes, the template 310 be temporarily affixed to the pipe P using only the coarsely threaded wood screws 335. As best seen in FIGS. 38 and 39, if the U-bolts 501 and 503 are not used to secure the template 310 to the pipe P, the pairs of nuts 521 and 523 are tightened to secure the U-bolts 521 and 523 to the template 310 with the cross-portions of the bolts 501 and 503 seated in their respective recesses 515 and 517. The depth of the recesses 515 and 517 is sufficient to afford clearance for the cross-portions of the bolts 501 and 503 when the pipe P is fully seated against the contour of the base 311 of the template 310.

The coupon defining array need not be symmetric around the tangential axis in this coupon arrangement. If the tangential axis is still placed in the plane of interface of the fused joint, where a sample is being produced from a fused joint and not from base pipe, the tensile load application holes need not be symmetrical about the tangential axis, although they will still straddle this axis.

If the width of the reduced section in the base pipe material is at least "X" times the width of the reduced section placed in the joint interface, the strength of the joint is at least "X" times the strength of the base pipe.

Method for Producing Asymmetric Coupons

Looking at FIGS. 40-45, the method for producing a tensile test coupon 380 from a plastic pipe P involves the steps of drilling an array of holes 621, 622 and 623 through the wall of the pipe P to define a straight-line-connectable point-to-point pattern 625 for the coupon 380, drilling at least two additional holes 631 through the wall of the pipe P within the pattern 625 of the coupon 80 for facilitating application of tensile force to the coupon 380 at its narrowest cross-section 681 and making straight line cuts 641, 643, and 645 with a reciprocating saw, the cuts 641, 643 and 645 connecting the array of holes 621, 622 and 623 in the pattern 625 of the coupon 380 to separate the coupon 380 from the pipe P.

Using the template 310 of the present invention, the method can be applied with speed and accuracy in the field. At the geographic location of the fusion process, the method involves the steps of laying the template 310 on the outer surface of the pipe P, using the template holes 321, 322, 323 and 331 to guide the drilling of an array of coupon holes 621, 622 and 623 through the wall of the pipe P and additional holes 395 through the pipe P. The template 310 is removed from the pipe P and the cuts 641, 643, and 645 are made to connect the pattern holes 621, 622 and 623 in the coupon 380. Before drilling, the template 310 can be secured to the outer surface of the pipe P, as by driving screws 335 through the template screw mounting holes 333 or using U-bolts 501 and 503 inserted through the pairs of template bolt holes 505 and 507 and secured with nuts 521 and 523.

In the laying step, the V-groove 313 aligns the template 310 and pipe longitudinal axes 315 and L. If the coupon 380 is to be taken at a fusion joint J of the pipe P, the template holes 321 are visually aligned at their narrowest cross-section 381 on the plane of the fusion interface between the fusion beads B which lie in the relief 319 on the template 310. In the securing step, a screwdriver can be used to install coarsely threaded wood screws 335 through the mounting holes 333 of the template 310 into the pipe P to be tested or a wrench used to tighten the nuts 521 and 523 on the U-bolts 501 and 503. The screws 335 or bolts 501 and 503 firmly, but temporarily, attach the template 310 to the outer surface of the pipe P. A hand drill with a bit of appropriate diameter to accommodate the width of a reciprocating saw blade is used to drill through the template holes 321, 322 and 323 and tensile force 331 holes and into the pipe P to create the coupon pattern holes 621, 622 and 623 and tensile force holes 631. A twist drill bit of diameter and length of flute to evacuate the drilled pipe chips and shavings out the upper side of the template 310 when fully engaged with the pipe P is preferred for drilling through the holes 321, 322, 323 and 331 and into the pipe P. The template guides the bit through the hardened drill bushings 329 and into and through the wall of the pipe P. The screwdriver or wrench are again used to unthread the wood screws 335 from the pipe P or remove the nuts 521 and 523 from the bolts 501 and 503 and remove the template 310. A hand held reciprocating saw can be used to make cuts 641, 643 and 645 which connect the outer or coupon pattern holes 621, 622 and 623 in the pipe P, leaving the pin and clevis holes 631 within the confines of the coupon 380 intact and separating the coupon 380 to be tested from the pipe P. Preferably, the bow-tie-knot cuts 641 and the saw cuts 643 are made in the pipe P and then two final cuts 645 are made between the corner holes 623 parallel to the plane of fusion between the beads B, the final cuts 645 freeing the coupon 380 from the pipe P. The coupon 380 is ready to be loaded into an on on-site tensile testing device such as a manually pumped, hydraulically actuated tensile testing machine, suitable for field use by a single operator. The operator then removes the coupon 380 from the tensile testing apparatus and inspects the surfaces of failure, making a determination of the quality of the joint J on the basis of comparison to a base pipe failure prepared using the same template 310 and method, or on the basis of other pre-determined criteria. Thus, using the tools above described, the entire test process can be accomplished on-site by a single operator.

Thus, it is apparent that there have been provided in accordance with the invention a method and template for producing a tensile test coupon that fully satisfy the objects, aims and advantages set forth above. While the invention has been described in conjunction with specific embodiments thereof, it is evident that many alternatives, modifications and variations will be apparent to those skilled in the art and in light of the foregoing description. Accordingly, it is intended to embrace all such alternatives, modifications and variations as fall within the spirit of the appended claims.

What is claimed is:

1. For use in producing a tensile test coupon from a plastic pipe, a template comprising:
   a plate having a contour for stable abutment against an outer surface of the pipe;
   an array of holes through said plate, said array of holes defining a straight-line-connectable bow-tie-like pattern for the coupon, a bow-tie-knot portion of said pattern being defined by two holes of said array;
   at least two additional holes through said plate within said pattern, said additional holes being oriented to locate sites on the coupon for application of tensile force to the coupon at a narrowest cross-section of said bow-tie-knot portion of said pattern; and
   two pairs of holes through said plate, each said pair being outside of and straddling said pattern, said pairs of holes being oriented to receive U-bolts therethrough securing said plate contour against the pipe.

2. A template according to claim 1, said array of holes being symmetrically arranged in relation to a pair of intersecting axes, one said axis being tangential to and another said axis being longitudinal along said outer surface of the pipe when said plate is in stable abutment against the pipe.

3. A template according to claim 2, said at least two additional holes being symmetrically displaced from said tangential axis and lying on said longitudinal axis.

4. A template according to claim 3, said plate having a relief for receiving beads formed on the outer surface of the pipe by fusion of the pipe along a plane-of-fusion interface thereof with said tangential axis lying in a plane of the interface.

5. A template according to claim 4, each said pair of holes symmetrically straddling said longitudinal axis and lying on axes parallel to said tangential axis.

6. A template according to claim 5, each said pair of holes being within said relief and symmetrically displaced from said tangential axis.

7. A template according to claim 6, said relief having recesses therein for containing cross-portions of the U-bolts fully inserted into their respective pairs of holes.

8. A template according to claim 1, said contour comprising a V-groove aligning said longitudinal axis of said plate with the longitudinal axis of the pipe.

9. A template according to claim 8, said V-groove being step-tapered.

10. A template according to claim 1 further comprising a third pair of holes through said plate, said third pair being outside of and on lengthwise opposite ends of said pattern to receive screws therethrough securing said plate contour against the pipe.

11. For use in producing a tensile test coupon from a plastic pipe, a template comprising:
    a plate having a contour for stable abutment against an outer surface of the pipe;
    an array of holes through said plate, said array of holes defining a straight-line-connectable bow-tie-like pattern for the coupon, a bow-tie-knot portion of said pattern being defined by four holes of said array; and
    at least two additional holes through said plate within said pattern, said additional holes being oriented to locate sites on the coupon for application of tensile force to the coupon at a narrowest cross-section of said bow-tie-knot portion of said pattern.

12. A template according to claim 11, said array of holes being symmetrically arranged in relation to a pair of intersecting axes, one said axis being tangential to and another said axis being longitudinal along said outer surface of the pipe when said plate is in stable abutment against the pipe.

13. A template according to claim 12, said at least two additional holes being symmetrically displaced from said tangential axis and lying on said longitudinal axis.

14. A template according to claim 13, said plate having a relief for receiving beads formed on the outer surface of the pipe by fusion of the pipe along a plane-of-fusion interface thereof, said four holes being aligned two on each side of said tangential axis with said relief aligned with two of said four holes on one side of said tangential axis.

15. A template according to claim 11, said contour comprising a V-groove aligning said longitudinal axis of said plate with the longitudinal axis of the pipe.

16. A template according to claim 15, said V-groove being step-tapered.

17. A template according to claim 11 further comprising a pair of holes through said plate, said pair being outside of and on lengthwise opposite ends of said pattern to receive screws therethrough securing said plate contour against the pipe.

18. For use in producing a tensile test coupon from a plastic pipe, a template comprising:
    a plate having a contour for stable abutment against an outer surface of the pipe;
    an array of holes through said plate, said array of holes defining a straight-line-connectable bow-tie-like pattern for the coupon, a bow-tie-knot portion of said pattern being defined by four holes of said array;
    at least two additional holes through said plate within said pattern, said additional holes being oriented to locate sites on the coupon for application of tensile force to the coupon at a narrowest cross-section of said bow-tie-knot portion of said pattern; and
    two pairs of holes through said plate, each said pair being outside of and straddling said pattern, said pairs of holes being oriented to receive U-bolts therethrough securing said plate contour against the pipe.

19. A template according to claim 18, said array of holes being symmetrically arranged in relation to a pair of intersecting axes, one said axis being tangential to and another said axis being longitudinal along said outer surface of the pipe when said plate is in stable abutment against the pipe.

20. A template according to claim 19, said at least two additional holes being symmetrically displaced from said longitudinal axis and lying on said tangential axis.

21. A template according to claim 20, said plate having a relief for receiving beads formed on the outer surface of the pipe by fusion of the pipe along a plane-of-fusion interface thereof, said four holes being aligned two on each side of said tangential axis with said relief aligned with two of said four holes on one side of said tangential axis.

22. A template according to claim 21, each said pair of holes symmetrically straddling said longitudinal axis and lying on axes parallel to said tangential axis.

23. A template according to claim 22, one said pair of holes being within said relief.

24. A template according to claim 23, said plate having recesses therein for containing cross-portions of the U-bolts fully inserted into their respective pairs of holes.

25. A template according to claim 18, said contour comprising a V-groove aligning said longitudinal axis of said plate with the longitudinal axis of the pipe.

26. A template according to claim 25, said V-groove being step-tapered.

27. A template according to claim 18 further comprising a third pair of holes through said plate, said third pair being outside of and on lengthwise opposite ends of said pattern to receive screws therethrough securing said plate contour against the pipe.

28. For producing a tensile test coupon from a plastic pipe, a method comprising the steps of:

laying a template on an outer surface of the pipe, the template having an array of holes therethrough defining a straight-line-connectable bow-tie-like pattern for the coupon, at least two additional holes within the pattern of the coupon and oriented to facilitate application of tensile force to the coupon at a narrowest cross-section of the coupon and two pairs of holes outside of and straddling said pattern;

securing the template against the pipe using U-bolts through the two pairs of holes;

drilling through the array of holes and the additional holes in the template into the pipe to provide matching holes through a wall of the pipe;

removing the template from the pipe;

making straight line cuts with a reciprocating saw, the cuts connecting the array holes in the pipe in the pattern of the coupon to separate the coupon from the pipe.

\* \* \* \* \*